United States Patent [19]
Norris

[11] 3,957,840
[45] May 18, 1976

[54] PREPARATION OF A FERROCENYL COMPOUND

[75] Inventor: William P. Norris, Ridgecrest, Calif.

[73] Assignee: The United States of America as represented by the Secretary of the Navy, Washington, D.C.

[22] Filed: July 15, 1974

[21] Appl. No.: 488,872

[52] U.S. Cl. ................ 260/439 CY; 260/429 CY
[51] Int. Cl.² ............................................ C07F 15/02
[58] Field of Search ........................... 260/439 CY

[56] References Cited
UNITED STATES PATENTS

| | | | |
|---|---|---|---|
| 2,709,175 | 5/1955 | Graham | 260/439 CY |
| 3,217,019 | 11/1965 | De Young | 260/439 CY |
| 3,577,449 | 5/1971 | Ashmore | 260/439 CY |
| 3,598,850 | 8/1971 | Dewey | 260/439 CY |
| 3,739,004 | 6/1973 | Ponder et al. | 260/439 CY |
| 3,751,441 | 8/1973 | Van Landuyt | 260/439 CY |
| 3,770,786 | 11/1973 | Huskins et al. | 260/439 CY |
| 3,878,233 | 4/1975 | Nielson | 260/439 CY |

FOREIGN PATENTS OR APPLICATIONS

| | | |
|---|---|---|
| 613,806 | 1/1961 | Canada |
| 704,600 | 3/1965 | Canada |

OTHER PUBLICATIONS

Rosenblum, Chemistry of the Iron Group Metallocenes, Interscience Publ., N.Y., pp. 125 to 128 (1965).

*Primary Examiner*—Helen M. S. Sneed
*Attorney, Agent, or Firm*—R. S. Sciascia; Roy Miller; Lloyd E. K. Pohl

[57] ABSTRACT

4,4-Diferrocenylpentanol is prepared by reacting 3-acetyl-1-propanol with ferrocene in a methylene chloride solvent and in the presence of catalytic amounts of trifluoroacetic acid. The compound is useful as a burning rate modifier for rocket propellants.

2 Claims, No Drawings

PREPARATION OF A FERROCENYL COMPOUND

BACKGROUND OF THE INVENTION

1. Field of the Invention

This invention relates to a method for the preparation of the ferrocene derivative 4,4-Diferrocenylpentanol.

2. Description of the Prior Art 4,4-Diferrocenylpentanol has been prepared before. The prior art preparation is a three step process involving the reaction of methyl levulinate with ferrocene to produce 4,4-Diferrocenylpentanoate, separating the 4,4-Diferrocenylpentanoate from side products and, finally, reacting 4,4-Diferrocenylpentanoate with lithium aluminum hydride to produce the alcohol. The prior art process is somewhat cumbersome in that the separation step is difficult to carry out and in that lithium aluminum hydride is a difficult material to handle. It would, therefore, be advantageous if a simpler method for the preparation of 4,4-Diferrocenylpentanol existed.

SUMMARY OF THE INVENTION

According to this invention, 4,4-Diferrocenylpentanol is prepared, in what is essentially a one step process, by reacting 3-acetyl-1-propanol with ferrocene in methylene chloride solvent and in the presence of catalytic amounts of trifluoroacetic acid.

DESCRIPTION OF THE PREFERRED EMBODIMENT

The preferred embodiment of this invention may be conveniently described by one specific example.

EXAMPLE

Ten grams (0.054 mole) of ferrocene and 1.02 g. (0.0100 mole) of 3-acetyl-1-propanol were dissolved in 40 ml of methylene chloride. Ten mililiters of trifluoroacetic acid was then added with stirring. The reaction mixture darkened and warmed to the touch when the acid was added. The reaction mixture was allowed to stand at ambient condition for 2 hours and 20 minutes. Fifty mililiters of water was added with stirring. The blue color of the aqueous phase was discharged with a small amount of ascorbic acid. The methylene chloride phase was separated and poured onto an activated alumina column (50mm × 250mm). Unreacted ferrocene, 7.6 g, was eluted with methylene chloride. The next band, moving more slowly than the ferrocene band, contained the desired product. Elution was stopped and this band of the column was separated and extracted with methanol to give 2.8 g, 62% yield of 4,4-Diferrocenylpentanol-1. Recrystallization from cyclohexane gave 2.0 g of red-brown crystals, m.p. 112°–113°.

Anal. Calcd. for $C_{25}H_{28}Fe_2O$: C, 65.82; H, 6.19; Fe, 24.49; Found: C, 65.44; H, 6.14; Fe, 24.81.

The reaction may also be worked up by evaporating the methylene chloride and heating the residue to 100°C at less than 1 mm pressure to sublime out the unreacted ferracene. The remaining material is recrystallized from cyclohexane to give the product 4,4-Diferracenylpentanol-1.

Ten mililiters of trifluoroacetic acid are specified for about 1 gram (1.02 g) of 3-acetyl-1-propanol reactant in the foregoing example. Less trifluooacetic acid can be used. The use of less trifluoroactic acid catalyst may, however, slow the reaction and the reaction time allowed will have to be adjusted accordingly.

In the foregoing example an excess of ferrocene is specified (0.054 mole per 0.01 mole of 3-acetyl-1-propanol). Since only two ferrocenyl groups are put on each propanol group in the reaction, it will be apparent to those skilled in the art that the excess of ferrocene need not be so large as that used in the example. However, it is preferable to use some excess of ferrocene.

It will be apparent to those skilled in the art that the reaction time (2 hours 20 minutes) could be varied somewhat. 4,4-Diferrocenylpentanol may be tied into a solid rocket propellant for use as a burning rate catalyst in the by now well known way wherein the hydroxy group of the ferrocene derivative is reacted with an isocyanate group of an isocyanate curing agent during propellant workup.

What is claimed is:

1. A method for preparing 4,4-diferrocenylpentanol comprising the steps of:
    a. dissolving 3-acetyl-1-propanol and ferrocene in methylene chloride to form a solution;
    b. adding trifluroacetic acid to the solution in an amount sufficient to provide about 10 mililiters of trifluoroactic acid for every 10 grams of ferrocene in the solution; and
    c. allowing the 3-acetyl-1-propanol and ferrocene in the solution to react under the catalytic influence of the trifluoroacetic acid.

2. A method according to claim 1 wherein an excess of ferrocene is used and about 10 ml of trifluoroacetic acid are added for every 0.01 mole of 3-acetyl-1-propanol.

* * * * *